US006670135B1

(12) United States Patent
Spriggs

(10) Patent No.: US 6,670,135 B1
(45) Date of Patent: Dec. 30, 2003

(54) SEMAPHORIN POLYPEPTIDES

(75) Inventor: Melanie K. Spriggs, Seattle, WA (US)

(73) Assignee: Immunex Corporation, Seattle, WA (US)

( * ) Notice: Subject to any disclaimer, the term of this patent is extended or adjusted under 35 U.S.C. 154(b) by 36 days.

(21) Appl. No.: 09/689,012

(22) Filed: Oct. 12, 2000

Related U.S. Application Data

(63) Continuation of application No. PCT/US99/09831, filed on May 5, 1999.
(60) Provisional application No. 60/085,497, filed on May 14, 1998.

(51) Int. Cl.[7] .................. C12N 15/00; C12N 16/63; C07H 21/04; G01N 33/53; C07K 14/00
(52) U.S. Cl. .................. 435/7.1; 435/69.1; 435/188; 435/235.1; 435/325; 435/375; 435/320.1; 435/7.2; 530/300; 530/350; 536/23.1; 536/23.5
(58) Field of Search .................. 435/7.2, 7.1, 69.1, 435/188, 235.1, 325, 375, 320.1; 530/300, 350; 536/23.1, 23.5

(56) References Cited

U.S. PATENT DOCUMENTS 6,225,285 B1   5/2001   Luo et al. ............... 514/12

FOREIGN PATENT DOCUMENTS

EP    0 933 425 A1    8/1999
WO    WO 99/45114    9/1999

OTHER PUBLICATIONS

Ensser, Armin and Fleckenstein, Bernhard, "Alcelaphine herpesvirus type 1 has a semaphorin–like gene," *J. Gen. Virol.* 76: 1063–1067, 1995.

Lange, C. et al., "New eukaryotic semaphorins with close homology to semaphorins of DNA viruses," *Genomics 51*: 340–350, 1998.

Xu, X. et al., "Human semaphorin K1 is glycosylphosphatidylinositol–linked and defines a new subfamily of viral–related semaphorins," *J. Biol. Chem.* 273(35): 22428–22434, 1998.

Yamada, A. et al. "Molecular cloning of a glycosylphosphatidylinositol–anchored molecule CDw108," *J. Immunol.* 162: 4094–4100, 1999.

*Primary Examiner*—Gary Kunz
*Assistant Examiner*—Virmal S. Basi
(74) *Attorney, Agent, or Firm*—Janis C. Henry; Kathleen Fowler

(57) ABSTRACT

This invention provides a method comprising assaying the binding of a DCSema polypeptide to a VESPR protein.

9 Claims, No Drawings

SEMAPHORIN POLYPEPTIDES

RELATED APPLICATIONS

This application is a continuation of International application PCT/US99/09831 filed May 5, 1999 which claims the benefit of U.S. Provisional Application No. 60/085,497 filed May 14, 1998.

FIELD OF THE INVENTION

The present invention relates to semaphorin polypeptides, nucleic acids encoding such semaphorin polypeptides, processes for producing recombinant semaphorin polypeptides, pharmaceutical compositions containing such polypeptides relates and processes for treating disorders associated with semaphorin activity.

BACKGROUND OF THE INVENTION

The semaphorin gene family includes a large number of molecules that encode related transmembrane and secreted glycoproteins known to be neurologic regulators. The semaphorins are generally well conserved in their extracellular domains which are typically about 500 amino acids in length. Semaphorin family proteins have been observed in neuronal and nonneuronal tissue and have been studied largely for their role in neuronal growth cone guidance. For example, the secreted semaphorins known as collapsin-1 and Drosophila semaphorin II are selectively involved in repulsive growth cone guidance during development. Flies having semaphorin II genes that are mutated so that their function is reduced exhibit abnormal behavior characteristics.

Another semaphorin gene has been identified in several strains of poxvirus. This semaphorin is found in vaccinia virus (Copenhagen strain) and Ectromelia virus, and is encoded in an open reading frame (ORF) known as A39R. The A39R encoded protein has no transmembrane domain and no potential membrane linkage and is known to be a secreted protein. Variola virus ORF also contains sequences that share homology with the vaccinia virus ORF A39R at the nucleotide level and the amino acid level. Another viral semaphorin. AHV-sema, has been found in the Alcelaphine Herpesvirus (AHV).

Genes encoding mammalian (human, rat, and mouse) semaphorins have been identified, based upon their similarity to insect semaphorins. Functional studies of these semaphorins suggest that embryonic and adult neurons require a semaphorin to establish workable connections. Significantly, the fast response time of growth cone cultures to appropriate semaphorins suggests that semaphorin signaling involves a receptor-mediated signal transduction mechanism. Semaphorin ligands that are secreted into the extracellular milieu signal through receptor bearing cells in a located and systemic fashion. In order to further investigate the nature of cellular processes regulated by such local and systemic signaling, it would be beneficial to identify additional semaphorin receptors and ligands. Furthermore, because virus encoded semaphorins are produced by infected cells and are present in viruses that are lytic (poxviruses) and viruses that are not known to be neurotropic (AHV), it is unlikely that their primary function is to modify neurologic responses. It is more likely that the virus encoded semaphorins function to modify the immunologic response of the infected host and it is likely that mammalian homologous to virus encoded semaphorins function to modify the immunologic response. In view of the suggestion that viral semaphorins may function in the immune system as natural immunoregulators it would be beneficial to identify semaphorins that may be therapeutic agents for enhancing or diminishing the immune response.

SUMMARY OF THE INVENTION

The present invention pertains to novel semaphorins as isolated or homogeneous proteins. In particular, the present invention provides semaphorin polypeptides, that are homologous to the viral semaphorins A39R and AHV Sema. Within the scope of the present invention are DNAs encoding semaphorin polypeptides and expression vectors that include DNA encoding semaphorin polypeptides. The present invention also includes host cells that have been transfected or transformed with expression vectors that include DNA encoding a semaphorin polypeptide, and processes for producing semaphorin polypeptides by culturing such host cells under conditions conducive to expressing semaphorin polypeptides. The present invention further includes antibodies directed against semaphorin polypeptides.

Further within the scope of the present invention are processes for purifying or separating certain novel semaphorin polypeptides or cells that express novel semaphorins to which semaphorin receptor polypeptides bind. Such processes include binding at least one semaphorin receptor to a solid phase matrix and contacting a mixture containing a semaphorin polypeptide to which the semaphorin receptor binds, or a mixture of cells expressing the semaphorin with the bound semaphorin receptor, and then separating the contacting surface and the solution.

The present invention additionally provides processes for treating mammals afflicted with a disease that is ameliorated by the interaction of semaphorins and their receptors. Such processes involve activating immune cells that express receptors for the semaphorins of the present invention and include administering a therapeutically effective amount of semaphorin to a mammal afflicted with the disease. The therapeutically effective amount is sufficient to activate immune system cells that express semaphorin receptors. Such an activation results in the secretion of cytokines, the regulation of activation antigens or the migration of the cell to sites of immune activity.

DETAILED DESCRIPTION OF THE INVENTION

The present invention provides novel semaphorin polypeptides, DNA encoding semaphorin polypeptides and recombinant expression vectors that include DNA encoding semaphorin polypeptides. The present invention further provides methods for isolating semaphorin polypeptides and methods for producing recombinant semaphorin polypeptides by cultivating host cells transfected with the recombinant expression vectors under conditions appropriate for expressing semaphorin and recovering the expressed semaphorin polypeptide.

This invention additionally provides antibodies directed against semaphorin polypeptides.

Particular semaphorin embodiments of the present invention include polypeptides homologous to AHV sema. The native semaphorin polypeptide described herein was discovered using data base search and comparison techniques that resulted in the identification of at least one EST having some homology to viral semaphorins. As described in Example 1, PCR techniques were used to identify and clone the full viral semaphorin homologue. The human semaphorin of the present invention is found in placenta, testis, ovary, spleen, dendritic cells, and B cells. Semaphorin polypeptides of the present invention bind to the semaphorin receptor, designated VESPR (described in copending application S/N 08/958,598, incorporated herein by reference). Evidence suggests that the interaction between the semaphorins of the present invention and their receptors are associated with the immune suppression of mature dendritic cells. For this reason, the semaphorins of the present invention are designated DCSema.

Example 1 describes identifying a native DCSema of the present invention. The amino acid sequence of the identified native DCSema is disclosed in SEQ ID NO:2 and the DNA encoding the amino acid sequence is disclosed in SEQ ID NO:1. The amino acid sequence presented in SEQ ID NO:2 is a secreted soluble polypeptide, but may additionally exist as a membrane bound protein. The amino acid sequence of SEQ ID NO:2 has a predicted signal sequence that includes amino acids 1–44. Also encompassed within the present invention are soluble DCSema polypeptides that lack the signal sequence. An example of such a polypeptide is amino acids 45–666 of SEQ ID NO:2. The EST 151129 portion of SEQ ID NO:2 has a 28% identity to A39R and 44% identity to AHV sema both of which bind to VESPR, a semaphorin receptor described in copending patent application Ser. No. 08/958,598. A39R and AHV sema share 29% identity.

The terms "semaphorin polypeptide", "human semaphorin homologue", "DCSema" and homologous of AHV Sema encompass polypeptides having the amino acid sequence disclosed in SEQ ID NO:2, and proteins that are encoded by nucleic acids that contain the nucleic acid sequence of SEQ ID NO:1. In addition, those polypeptides that have a high degree of similarity or a high degree of identity with the amino acid sequence of SEQ ID NO:2, which polypeptides are biologically active and bind at least one molecule or fragments of a molecule that is a semaphorin receptor. In addition, "semaphorin polypeptide", "human semaphorin homologue", "DCSema" refers to biologically active gene products of the DNA of SEQ ID NO:1. Further encompassed by semaphorin polypeptides are soluble or truncated proteins that comprise primarily the binding portion of the protein retain biological activity and are capable of being secreted. Specific examples of such soluble proteins are those comprising the sequence of amino acids 45–666 of SEQ ID NO:2.

The term "biologically active" as it refers to semaphorin polypeptides, means that the semaphorin polypeptide is capable of binding to at least one semaphorin receptor. Assays suitable for determining DCSema binding are described infra and can include standard flow cytometry tests and slide binding tests.

"Isolated" means a DCSema polypeptide is free of association with other proteins or polypeptides, for example, as a purification product of recombinant host cell culture or as a purified extract.

A DCSema polypeptide variant as referred to herein, means a polypeptide substantially homologous to native DCSema polypeptide but which has an amino acid sequence different from that of the native polypeptides because of one or more deletions, insertions or substitutions. The variant amino acid sequence preferably is at least 80% identical to a native DCSema amino acid sequence, most preferably at least 90% identical. The percent identity may be determined, for example, by comparing sequence information using the GAP computer program, version 6.0 described by Devereux et al. (Nucl. Acids Res. 12:387, 1984) and available from the University of Wisconsin Genetics Computer Group (UWGCG). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353–358. 1979; (2) a penalty of 3.0 for each gap and an additional 0.10 penalty for each symbol in each gap; and (3) no penalty for end gaps. Variants may comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics are well known. Naturally occurring variants or alleles are also encompassed by the invention. Examples of such variants are proteins that result from alternate mRNA splicing events or from proteolytic cleavage of the DCSema protein, wherein the binding property is retained. Alternate splicing of mRNA may yield a truncated but biologically active polypeptide, such as a naturally occurring soluble form of the protein for example. Variations attributable to proteolysis include, for example, differences in the N-termini upon expression in different types of host cells, due to proteolytic removal of one or more terminal amino acids from the DCSema polypeptide (generally from 1–5 terminal amino acids).

Example 3 describes the construction of a novel viral Semaphorin/Fc fusion (DCSema/Fc) protein that may be utilized in studying the biological characteristics of DCSema and their receptor distribution. Other antibody Fc regions may be substituted for the human IgG1 Fc region described in Example 3. Suitable Fc regions are those that can bind with high affinity to protein A or protein G, and include the Fc region of human IgG1 or fragments of the human or murine IgG1 Fc region, e.g., fragments comprising at least the hinge region so that interchain disulfide bonds will form. The viral DCSema/Fc fusion protein offers the advantage of being easily purified. In addition, disulfide bonds form between the Fc regions of two separate fusion protein chains, creating dimers.

The soluble DCSema polypeptides of the present invention may be isolated and identified by separating intact cells that express the desired protein from the culture medium in which the cells grow, and then assaying the medium (supernatant) for the presence of the desired protein. Separation can be accomplished using standard separation techniques including, including centrifugation. The presence of the DCSema polypeptide in the medium indicates that the protein was secreted from the cells in its expected soluble form. Because the DCSema polypeptides of the present invention are secreted soluble polypeptides they possess many advantages over membrane bound proteins. Purification of the proteins from recombinant host cells is feasible, since the soluble proteins are secreted from the cells. Further, soluble proteins are generally more suitable for intravenous administration.

Truncated DCSema proteins comprising less than the entire secreted polypeptide are included in the invention, e.g. soluble fragments such as amino acids 52–543 of SEQ ID NO:2 that include the "semaphorin domain," which is part of an active binding site, and amino acids 45–644 of SEQ ID NO:2 that include the secreted protein without the signal peptide, are included in the invention. When initially expressed within a host cell, DCSema polypeptides may additionally comprise one of the heterologous signal peptides described below that is functional within the host cells employed. Alternatively, the protein may comprise the native signal peptide. In one embodiment of the invention, DCSema polypeptides can be expressed as a fusion protein comprising (from N- to C-terminus) the yeast α-factor signal peptide, a FLAG® peptide described below and in U.S. Pat. No. 5,011,912, and soluble DCSema polypeptide consisting of amino acids 45 to 666 of SEQ ID NO:2. This recombinant fusion protein is expressed in and secreted from yeast cells. The FLAG® peptide facilitates purification of the protein, and subsequently may be cleaved from the DCSema using bovine mucosal enterokinase.

Truncated DCSema polypeptides may be prepared by any of a number of conventional techniques. A desired DNA sequence may be chemically synthesized using techniques known per se. DNA fragments also may be produced by restriction endonuclease digestion of a full length cloned DNA sequence and isolated by electrophoresis on agarose gels. Linkers containing restriction endonuclease cleavage site(s) may be employed to insert the desired DNA fragment into an expression vector, or the fragment may be digested at cleavage sites naturally present therein. The well known polymerase chain reaction procedure also may be employed to amplify a DNA sequence encoding a desired protein fragment. As a further alternative, known mutagenesis techniques may be employed to insert a stop codon at a desired point, e.g., immediately downstream of the codon for the last amino acid of the binding domain.

As stated above, the invention provides isolated or homogeneous DCSema polypeptides, both recombinant and non-recombinant. Varants and derivatives of native DCSema proteins that retain the desired biological activity (e.g., the ability to bind to DCSema receptors) may be obtained by mutations of nucleotide sequences coding for the native polypeptides. Alterations of the native amino acid sequence may be accomplished by any of a number of conventional methods. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene wherein predetermined codons can be altered by substitution, deletion or insertion. Exemplary methods of making the alterations set forth above Are disclosed by Walder et al. (*Gene* 42:133, 1986); Bauer et al. (*Gene* 37:73, 1985); Craik (*BioTechniques*, Jan. 1985, 12–19); Smith et al. (*Genetic Engineering: Principles and Methods*, Plenum Press, 1981); Kunkel (*Proc. Nail. Acad. Sci. USA* 82:488, 1985); Kunkel et al. (*Methods in Enzymol.* 154:367, 1987); and U.S. Pat. Nos. 4,518,584 and 4,737,462 all of which are incorporated by reference.

Native DCSema polypeptides may be modified to create DCSema derivatives by forming covalent or aggregative conjugates with other chemical moieties, such as glycosyl groups, lipids, phosphate, acetyl groups and the like. Covalent derivatives of the polypeptides may be prepared by linking the chemical moieties to functional groups on DCSema amino acid side chains or at the N-terminus or C-terminus of a DCSema polypeptide. Other derivatives of the polypeptides within the scope of this invention include covalent or aggregative conjugates of DCSema polypeptides or their fragments with other proteins or polypeptides, such as by synthesis in recombinant culture as N-terminal or C-terminal fusions. For example, the conjugate may comprise a signal or leader polypeptide sequence (e.g. the α-factor leader of Saccharomyces) at the N-terminus of a polypeptide of the present invention. The signal or leader peptide co-translationally or post-translationally directs transfer of the conjugate from its site of synthesis to a site inside or outside of the cell membrane or cell wall.

DCSema polypeptide fusion proteins can comprise peptides added to facilitate purification and identification of semaphorin receptors that bind semaphorins of the present invention, including VESPR (see copending application Ser. No. 08/958,598. Such peptides include for example, poly-His or the antigenic identification peptides described in U.S. Pat. No. 5,011,912 and in Hopp et al., *Bio/Technology* 6:1204, 1988.

The invention further includes DCSema polypeptides with or without associated native-pattern glycosylation. DCSema polypeptide expressed in yeast or mammalian expression systems (e.g., COS-7 cells) may be similar to or significantly different from a native DCSema polypeptide in molecular weight and glycosylation pattern, depending upon the choice of expression system. Expression of DCSema polypeptides in bacterial expression systems, such as *E. coli*, provides non-glycosylated molecules.

Equivalent DNA constructs that encode various additions or substitutions of amino acid residues or sequences, or deletions of terminal or internal residues or sequences not needed for biological activity or binding are encompassed by the invention.

For example. N-glycosylation sites in the DCSema extracellular domain can be modified to preclude glycosylation, allowing expression of a reduced carbohydrate analog in mammalian and yeast expression systems. N-glycosylation sites in eukaryotic polypeptides are characterized by an amino acid triplet Asn-X-Y, wherein X is any amino acid except Pro and Y is Ser or Thr. The native human DC Sema of the present invention comprises 4 such amino acid triplets, at amino acids 105–107, 157–159, 258–260 and 602–604 of SEQ ID NO:2. Appropriate substitutions, additions or deletions to the nucleotide sequence encoding these triplets will result in prevention of attachment of carbohydrate residues at the Asn side chain. Alteration of a single nucleotide, chosen so that Asn is replaced by a different amino acid, for example, is sufficient to inactivate an N-glycosylation site. Known procedures for inactivating N-glycosylation sites in proteins include those described in U.S. Pat. 5,071,972 and EP 276,846, hereby incorporated by reference.

In another example, sequences encoding Cys residues that are not essential for biological activity can be altered to cause the Cys residues to be deleted or replaced with other amino acids, preventing formation of incorrect intramolecular disulfide bridges upon renaturation. Other equivalents are prepared by modification of adjacent dibasic amino acid residues to enhance expression in yeast systems in which KEX2 protease activity is present. EP 212,914 discloses the use of site-specific mutagenesis to inactivate KEX2 protease processing sites in a protein. KEX2 protease processing sites are inactivated by deleting, adding or substituting residues to alter Arg-Arg, Arg-Lys, and Lys-Arg pairs to eliminate the occurrence of these adjacent basic residues. Lys-Lys pairings are considerably less susceptible to KEX2 cleavage, and conversion of Arg-Lys or Lys-Arg to Lys-Lys represents a conservative and preferred approach to inactivating KEX2 sites. The DC sema of SEQ ID NO:2 contains 7 KEX2 protease processing sites at amino acids 123–124, 135,136, 192,193, 204–205, 460–461, 474–475 and 475–476, Nucleic acid sequences within the scope of the invention include isolated DNA and RNA sequences that hybridize to DCSema nucleotide sequences disclosed herein under conditions of moderate or high stringency, and that encode biologically active DCSema. Conditions of moderate stringency, as defined by Sambrook et al. *Molecular Cloning: A Laboratory Manual*, 2 ed. Vol. 1, pp. 101–104, Cold Spring Harbor Laboratory Press, (1989), include use of a prewashing solution of 5 X SSC, 0.5% SDS, 1.0 mM EDTA (pH 8.0) and hybridization conditions of about 55° C., 5 X SSC, overnight. Conditions of severe stringency include higher temperatures of hybridization and washing. The skilled artisan will recognize that the temperature and wash solution salt concentration may be adjusted as necessary according to factors such as the length of the nucleic acid molecule and the relative amount of A, T/U, C and G nucleotides.

Due to the known degeneracy of the genetic code wherein more than one codon can encode the same amino acid, a DNA sequence may vary from that shown in SEQ ID NO:1 and still encode a polypeptide having the amino acid sequence of SEQ ID NO:2. Such variant DNA sequences may result from silent mutations (e.g., occurring during PCR amplification), or may be the product of deliberate mutagenesis of a native sequence.

The invention provides equivalent isolated DNA sequences encoding biologically active human DCSema, selected from: (a) cDNA comprising the nucleotide sequence presented in SEQ ID NO:1; (b) DNA capable of hybridization to a DNA of (a) under moderately stringent conditions and that encodes biologically active polypeptides and (c) DNA that is degenerate as a result of the genetic code to a DNA defined in (a), or (b) and that encodes biologically active human DCSema polypeptide. Polypeptides encoded by such DNA equivalent sequences are encompassed by the invention.

DNAs that are equivalent to the DNA sequence of SEQ ID NO:1 include those that hybridize under moderately and highly stringent conditions to the DNA sequence that encodes polypeptides comprising the sequence of SEQ ID NO:2. Examples of proteins encoded by such DNA, include, but are not limited to polypeptide fragments and proteins that have inactivated N-glycosylation site(s), inactivated KEX2 protease processing site(s), or conservative amino acid substitution(s), as described above. DCSema polypeptides encoded by DNA derived from other species, wherein the DNA will hybridize to the cDNA of SEQ ID NO:1, are also within the present invention.

DCSema polypeptide variants possessing the ability to bind semaphorin receptors may be identified by any suitable assay. Biological activity of DCSema polypeptides of the present invention may be determined, for example, by competition for binding to the binding domain of semaphorin receptors, e.g. competitive binding assays, or for binding to a semaphorin receptor binding domain.

One type of a competitive binding assay for a DCSema polypeptide of the present invention uses a radiolabeled DCSema and intact semaphorin receptor-expressing cells. Instead of intact cells, one could substitute soluble semaphorin receptor:Fc fusion proteins bound to a solid phase through the interaction of a Protein A, Protein G or an antibody to the semaphorin receptor or Fc portions of the molecule, with the Fc region of the fusion protein. Competitive binding assays can be performed following conventional methodology. In one embodiment, a soluble semaphorin receptor can be made to compete with an immobilized receptor for binding with a soluble semaphorin ligand. For example, a radiolabeled soluble semaphorin ligand can be antagonized by soluble VESPR in an assay for binding activity against a surface-bound semaphorin receptor. Qualitative results can be obtained by competitive autoradiographic plate binding assays, or Scatchard plots may be utilized to generate quantitative results.

Alternatively, semaphorin binding proteins, such as VESPR or anti-semaphorin antibodies, can be bound to a solid phase such as a column chromatography matrix or a similar substrate suitable for identifying, separating or purifying cells that express semaphorin on their surface. Binding of a semaphorin-binding protein to a solid phase contacting surface can be accomplished by any means, for example, by constructing a VESPR:Fc fusion protein and binding such to the solid phase through the interaction of Protein A or Protein G. Various other means for fixing proteins to a solid phase are well known in the an and are suitable for use in the present invention. For example, magnetic microspheres can be coated with VESPR and held in the incubation vessel through a magnetic field. Suspensions of cell mixtures containing semaphorin-expressing cells are contacted with the solid phase that has VESPR polypeptides thereon. Cells having semaphorin on their surface bind to the fixed VESPR and unbound cells then are washed away. This affinity-binding method is useful for purifying, screening or separating such semaphorin-expressing cells from solution. Methods of releasing positively selected cells from the solid phase are known in the art and encompass, for example, the use of enzymes. Such enzymes are preferably non-toxic and non-injurious to the cells and are preferably directed to cleaving the cell-surface binding partner. In the case of semaphorin-VESPR interactions, the enzyme preferably would cleave the semaphorin, thereby freeing the resulting cell suspension from the "foreign" semaphorin receptor material. The purified cell population then may be used to repopulate mature (adult) tissues.

Alternatively, mixtures of cells suspected of containing semaphorin cells first can be incubated with a suitable biotinylated semaphorin receptor, e.g. VESPR. Incubation periods are typically at least one hour in duration to ensure sufficient binding to semaphorin The resulting mixture then is passed through a column packed with avidin-coated beads, whereby the high affinity of biotin for avidin provides the binding of the cell to the beads. Use of avidin-coated beads is known in the art. See Berenson, et al. *J. Cell. Biochem.*, 10D:239 (1986). Washing unbound material and releasing the bound cells is performed using conventional methods.

As described above, cells expressing DCSema polypeptides of the present invention can be separated using a semaphorin receptor, e.g. VESPR. In an alternative method, VESPR, other suitable semaphorin receptors, or an extracellular domain or a fragment thereof can be conjugated to a detectable moiety such as $^{125}$I to detect semaphorin-expressing cells. Radiolabeling with $^{125}$I can be performed by any of several standard methodologies that yield a functional $^{125}$I-molecule labeled to high specific activity or an iodinated or biotinylated antibody against the semaphorin receptor. Another detectable moiety such as an enzyme that can catalyze a colorimetric or fluorometric reaction, biotin or avidin may be used. Cells to be tested for DCSema polypeptide-expression can be contacted with a suitable labeled receptor, e.g. VESPR. After incubation, unbound labeled receptor is removed and binding is measured using the detectable moiety.

The binding characteristics of DCSema polypeptides may also be determined using a conjugated semaphorin receptor (for example, $^{125}$I-semaphorin receptor:Fc) in competition assays similar to those described above. In this case, however, intact cells expressing DCSema polypeptide of the present invention, bound to a solid substrate, are used to measure the extent to which a sample containing a putative receptor variant competes for binding with a conjugated DCSema.

Other means of assaying for DCSema polypeptides of the present invention include the use of anti-DCSema antibodies, cell lines that proliferate in response to DCSema polypeptide, or recombinant cell lines that express DCSema and proliferate in the presence of a suitable semaphorin receptor.

The DCSema proteins disclosed herein also may be employed to measure the biological activity of any semaphorin receptor in terms of its binding affinity for its semaphorin ligand. As one example, DCSema polypeptides of the present invention may be used in determining whether biological activity is retained after modification of a semaphorin receptor (e.g., chemical modification, truncation, mutation, etc.). The biological activity of a semaphorin receptor thus can be ascertained before it is used in a research study, or in the clinic, for example.

DCSema polypeptides disclosed herein find use as reagents in "quality assurance" studies, e.g., to monitor shelf life and stability of a receptor to which the DCSema binds under different conditions. To illustrate, DCSema polypeptides of the present invention may be employed in a binding affinity study to measure the biological activity of a test semaphorin receptor that has been stored at different temperatures, or produced in different cell types. The binding affinity of the DCSema protein for the test receptor is compared to that of a standard or control semaphorin receptor to detect any adverse impact on biological activity of the test semaphorin receptor.

DCSema polypeptides described herein also find use as carriers for delivering agents attached thereto to cells expressing semaphorin receptors to which the semaphorin binds. As described in copending application Ser. No. 958,598, VESPR, to which a DCSema of the present invention binds, is expressed in lung epithelial cells, stroma, intestinal epithelial cells and lymphoma cells. DCSema polypeptides of the present invention can thus can be used to deliver diagnostic or therapeutic agents to these cells (or to other cell types found to express a suitable semaphorin receptor on cell surfaces) in in vitro or in vivo procedures.

Diagnostic and therapeutic agents that may be attached to a DCSema polypeptide of the present invention include, but are not limited to, drugs, toxins, radionuclides, chromophores, enzymes that catalyze a colorimetric or fluorometric reaction, and the like, with the particular agent being chosen according to the intended application. Examples of drugs include those used in treating various forms of cancer, e.g., nitrogen mustards such as L-phenylalanine nitrogen mustard or cyclophosphamide, intercalating agents such as cis-diaminodichloroplatinum, antimetabolites such as 5-fluorouracil, vinca alkaloids such as vincristine, and antibiotics such as bleomycin, doxorubicin, daunorubicin, and derivatives thereof. Among the toxins are ricin, abrin, diptheria toxin, *Pseudomonas aeruginoso* exotoxin A, ribosomal inactivating proteins, mycotoxins such as trichothecenes, and derivatives and fragments (e.g., single chains) thereof. Radionuclides suitable for diagnostic use include, but are not limited to, 123I, $^{131}$I, $^{99m}$Tc, $^{111}$In, and $^{76}$Br. Radionuclides suitable for therapeutic use include, but are not limited to, $^{131}$I, $^{211}$At, $^{77}$Br, $^{186}$Re, $^{188}$Re, $^{212}$Pb, $^{212}$Bi, $^{109}$Pd, $^{64}$Cu. and $^{67}$Cu.

Such agents may be attached to the DCSema of the present invention by any suitable conventional procedure. Semaphorin homologues of the present invention, being proteins, include functional groups on amino acid side chains that can be reacted with functional groups on a desired agent to form covalent bonds, for example. Alternatively, the protein or agent may be derivatized to generate or attach a desired reactive functional group. The derivatization may involve attachment of one of the bifunctional coupling reagents available for attaching various molecules to proteins (Pierce Chemical Company, Rockford, Ill.). A number of techniques for radiolabeling proteins are known. Radionuclide metals may be attached to the receptor by using a suitable bifunctional chelating agent, for example. Conjugates comprising molecules of the present invention and a suitable diagnostic or therapeutic agent (preferably covalently linked) are thus prepared. The conjugates are administered or otherwise employed in an amount appropriate for the particular application.

Another use of the DCSema polypeptides of the present invention is as a research tool for studying the role that the DCSema, in conjunction with semaphorin receptors to which it binds, may play in immune regulation and viral infection. The polypeptides of the present invention also may be employed in in vitro assays for detection of receptors to which it binds, e.g. VESPR, or the interactions thereof. Similarly, DCSema polypeptides of the present invention can be used as a research tool for studying the role that the ligand, in conjunction with its receptors, play in immune regulation.

Furthermore, it is known that administration of IL-12 to tumor bearing animals results in tumor regression and the establishment of a tumor-specific immune response. Thus, using a DCSema ligand to bind with VESPR in order to enhance or promote IL-12 can induce a curative immune response against aggressive micrometastasizing tumors.

VESPR, a semaphorin receptor, binds with a binding partner to downregulate expression of MHC Class II molecules and CD86, a co-stimulatory molecule, on dendritic cells, cultured with GM-CSF and IL-4 (see copending application Ser. No. 60/085,497). By analogy, this suggests that the interaction between DCSema of the present invention and its receptors are associated with the immune suppression of mature dendritic cells. Thus, the use of DCSema ligands, including the DC Sema of the present invention, in the treatment of autoimmune disorders is expected to diminish unwanted symptoms associated with the autoimmune disorder by downregulating the antigen presenting capabilities of mature dendritic cells.

DCSema polypeptides of the invention can be formulated according to known methods used to prepare pharmaceutically useful compositions. The molecules of the invention can be combined in admixture, either as the sole active material or with other known active materials, with pharmaceutically suitable diluents (e.g., Tris-HCl, acetate, phosphate), preservatives (e.g., Thimerosal, benzyl alcohol, parabens), emulsifiers, solubilizers, adjuvants and/or carriers. Suitable carriers and their formulations are described in Remington's Pharmaceutical Sciences, 16th ed. 1980, Mack Publishing Co. In addition, such compositions can contain DCSema polypeptide complexed with polyethylene glycol (PEG), metal ions, or incorporated into polymeric compounds such as polyacetic acid, polyglycolic acid, hydrogels, etc., or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance of DCSema. DCSema polypeptides described herein can be conjugated to antibodies against tissue-specific receptors, ligands or antigens, or coupled to ligands of tissue-specific receptors.

DCSema polypeptides of the present invention can be administered topically, parenterally, or by inhalation. The term "parenteral" includes subcutaneous injections, intravenous, intramuscular, intracisternal injection, or infusion techniques. These compositions will typically contain an effective amount of the polypeptide, alone or in combination with an effective amount of any other active material. Such dosages and desired drug concentrations contained in the compositions may vary depending upon many factors, including the intended use, patient's body weight and age, and route of administration. Preliminary doses can be determined according to animal tests, and the scaling of dosages for human administration can be performed according to art-accepted practices.

Polypeptides of the present invention may exist as oligomers, such as covalently-linked or non-covalently-linked dimers or trimers. Oligomers may be linked by disulfide bonds formed between cysteine residues on different DCSema molecules. In one embodiment of the invention, a dimer is created by fusing a DCSema to the Fc region of an antibody (e.g., IgG1) in a manner that does not interfere with binding of the DCSema to a semaphorin receptor-binding domain. The Fc polypeptide preferably is fused to the C-terminus of a DCSema General preparation of fusion proteins comprising heterologous polypeptides fused to various portions of antibody-derived polypeptides (including the Fc domain) has been described, e.g., by Ashkenazi et al. (*PNAS USA* 88:10535, 1991) and Byrn et al. (*Nature* 344:677, 1990), hereby incorporated by reference. A gene fusion encoding the DCSema/Fc fusion protein is inserted into an appropriate expression vector. DCSema/Fc fusion proteins are allowed to assemble much like antibody molecules, whereupon interchain disulfide bonds form between Fc polypeptides, yielding divalent. If fusion proteins are made with both heavy and light chains of an antibody, it is possible to form a DCSema oligomer with as many as four semaphorin regions. Alternatively, one can link two DCSemas with a peptide linker.

Suitable host cells for expression of DCSema polypeptides of this invention include prokaryotes, yeast or higher eukaryotic cells. Appropriate cloning and expression vectors for use with bacterial, fungal, yeast, and mammalian cellular hosts are described, for example, in Pouwels et al. *Cloning Vectors: A Laboratory Manual*, Elsevier, N.Y., (1985). Cell-free translation systems could also be employed to produce the polypeptides of the present invention using RNAs derived from DNA constructs disclosed herein.

Prokaryotes include gram negative or gram positive organisms, for example, *E. coli* or Bacilli. Suitable prokaryotic host cells for transformation include, for example, *E. coli, Bacillus subtilis, Salmonella ryphimurium*, and various other species within the genera *Pseudomonas, Streptomyces*, and Staphylococcus. In a prokaryotic host cell, such as *E. coli*, a semaphorin receptor polypeptide may include an N-terminal methionine residue to facilitate expression of the recombinant polypeptide in the prokaryotic host cell. The N-terminal Met may be cleaved from the expressed recombinant DCSema polypeptide.

DCSema polypeptides may be expressed in yeast host cells, preferably from the Saccharomyces genus (e.g., *S. cerevisiae*). Other genera of yeast, such as Pichia, *K. lactis* or Kluyveronyces, may also be employed. Yeast vectors will often contain an origin of replication sequence from a 2 μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Hitzeman, EPA-73,657 or in Fleer et. al., *Gene*, 107:285–195 (1991); and van den Berg et. al., *Bio/Technology*, 8:135–139 (1990). Another alternative is the glucose-repressible ADH2 promoter described by Russell et al. (*J. Biol. Chem.* 258:2674, 1982) and Berg et al. (*Nature* 300:724, 1982). Shuttle vectors replicable in both yeast and *E. coli* may be constructed by inserting DNA sequences from pBR322 for selection and replication in *E. coli* (Amp$^r$ gene and origin of replication) into the above-described yeast vectors.

The yeast a-factor leader sequence may be employed to direct secretion of the VESPR or DCSema polypeptide. The α-factor leader sequence is often inserted between the promoter sequence and the structural gene sequence. See, e.g., Kurjan et al., *Cell* 30:933, 1982: Bitter et al., *Proc. Nail. Acad. Sci. USA* 81:5330, 1984; U.S. Pat. No. 4.546,082; and EP 324,274. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., *Proc. Nail. Acad Sci. USA* 75:1929. 1978. The Hinnen et al. protocol selects for Trp$^+$ transformants in a selective medium, wherein the selective medium consists of 0.67% yeast nitrogen base, 0.5% casamino acids, 2% glucose. 10 μg/ml adenine and 20 μg/ml uracil.

Yeast host cells transformed by vectors containing ADH2 promoter sequence may be grown for inducing expression in a "rich" medium. An example of a rich medium is one consisting of 1% yeast extract, 2% peptone, and 1% glucose supplemented with 80 μg/ml adenine and 80 μg/ml uracil. Depression of the ADH2 promoter occurs when glucose is exhausted from the medium.

Mammalian or insect host cell culture systems could also be employed to express recombinant polypeptides of the present invention. Baculovirus systems for production of heterologous proteins in insect cells are reviewed by Luckow and Summers, Bio/Technology 6:47 (1988). Established cell lines of mammalian origin also may be employed.

Examples of suitable mammalian host cell lines include the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells. HeLa cells, and BHK (ATCC CRL 10) cell lines, and the CV-1/EBNA-1 cell line derived from the African green monkey kidney cell line CVI (ATCC CCL 70) as described by McMahan et al. (*EMBO J*. 10: 2821, 1991).

Transcriptional and translational control sequences for mammalian host cell expression vectors may be excised from viral genomes. Commonly used promoter sequences and enhancer sequences are derived from Polyoma virus, Adenovirus 2, Simian Virus 40 (SV40), and human cytomegalovirus. DNA sequences derived from the SV40 viral genome for example, SV40 origin, early and late promoter, enhancer, splice, and polyadenylation sites may be used to provide other genetic elements for expression of a structural gene sequence in a mammalian host cell. Viral early and late promoters are particularly useful because both are easily obtained from a viral genome as a fragment which may also contain a viral origin of replication (Fiers et al., *Nature* 273:113, 1978). Smaller or larger SV40 fragments may also be used, provided the approximately 250 bp sequence extending from the Hind HI site toward the Bgl I site located in the SV40 viral origin of replication site is included.

Exemplary expression vectors for use in mammalian host cells can be constructed as disclosed by Okayama and Berg (*Mol. Cell. Biol*. 3:280, 1983). A useful system for stable high level expression of mammalian cDNAs in C127 murine mammary epithelial cells can be constructed substantially as described by Cosman et al. (*Mol. Immunol*. 23:935, 1986). A useful high expression vector, PMLSV N1/N4, described by Cosman et al., *Nature* 312:768, 1984 has been deposited as ATCC 39890. Additional useful mammalian expression vectors are described in EP-A-0367566, and in U.S. patent application Ser. No. 07/701,415, filed May 16, 1991, incorporated by reference herein. The vectors may be derived from retroviruses. In place of the native signal sequence, and in addition to an initiator methionine, a heterologous signal sequence may be added, such as the signal sequence for IL-7 described in U.S. Pat. No. 4,965,195: the signal sequence for IL-2 receptor described in Cosman et al., *Nature* 312:768 (1984); the IL-4 signal peptide described in EP 367,566; the type I IL-1 receptor signal peptide described in U.S. Pat. No. 4,968,607; and the type II IL-1 receptor signal peptide described in EP 20 460,846.

DCSema polypeptides of the present invention, as isolated, purified or homogeneous proteins may be produced by recombinant expression systems as described above or purified from naturally occurring cells. The polypeptides can be purified to substantial homogeneity, as indicated by a single protein band upon analysis by SDS-25 polyacrylamide gel electrophoresis (SDS-PAGE).

One process for producing polypeptides of the present invention comprises culturing a host cell transformed with an expression vector comprising a DNA sequence that encodes the desired DCSema polypeptide under conditions sufficient to promote expression of the DCSema polypeptide. The DCSema polypeptide is then recovered from culture medium or cell extracts, depending upon the expression system employed. As is known to the skilled artisan, procedures for purifying a recombinant protein will vary according to such factors as the type of host cells employed and whether or not the recombinant protein is secreted into the culture medium.

For example, when expression systems that secrete the recombinant protein are employed, the culture medium first may be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Finally, one or more reversed-phase high performance liquid chromatography (RP-HPLC) steps employing hydrophobic RP-HPLC media, (e.g., silica gel having pendant methyl or other aliphatic groups) can be employed to further purify the polypeptide. Some or all of the foregoing purification steps, in various combinations, are well known and can be employed to provide a substantially homogeneous recombinant protein.

It is possible to utilize an affinity column comprising the receptor-binding domain of a DCSema of the present invention affinity-purify semaphorin receptor to which the DCSema binds. Such a receptor can be removed from an affinity column using conventional techniques, e.g., in a high salt elution buffer and then dialyzed into a lower salt buffer for use or by changing pH or other components depending on the affinity matrix utilized.

Recombinant protein produced in bacterial culture can be isolated by initial disruption of the host cells, centrifugation, extraction from cell pellets if an insoluble polypeptide, or from the supernatant fluid if a soluble polypeptide, followed by one or more concentration, salting-out, ion exchange, affinity purification or size exclusion chromatography steps. Finally, RP-HPLC can be employed for final purification steps. Microbial cells can be disrupted by any convenient method, including freeze-thaw cycling, sonication, mechanical disruption, or use of cell lysing agents.

Transformed yeast host cells are preferably employed to express DCSemas of the present invention as a secreted polypeptide in order to simplify purification. Secreted recombinant polypeptide from a yeast host cell fermentation can be purified by methods analogous to those disclosed by Urdal et al. (*J. Chromatog*. 296:171, 1984). Urdal et al. describe two sequential, reversed-phase HPLC steps for purification of recombinant human IL-2 on a preparative HPLC column.

Useful fragments of the DCSema nucleic acids of the present invention include antisense or sense oligonucleotides comprising a single-stranded nucleic acid sequence (either RNA or DNA) capable of binding to target DCSema mRNA (sense) or DCSema DNA (antisense) sequences. Antisense or sense oligonucleotides, according to the present invention, comprise a fragment of the coding region of DCSema cDNA. Such a fragment generally comprises at least about 14 nucleotides, preferably from about 14 to about 30 nucleotides. The ability to derive an antisense or a sense oligonucleotide, based upon a cDNA sequence encoding a given protein is described in, for example. Stein and Cohen (Cancer Res. 48:2659, 1988) and van der Krol et al. (*BioTechniques* 6:958, 1988).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. The antisense oligonucleotides thus may be used to block expression of proteins of the present invention. Antisense or sense oligonucleotides further comprise oligonucleotides having modified sugar-phosphodiester backbones (or other sugar linkages, such as those described in WO91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences. Other examples of sense or antisense oligonucleotides include those oligonucleotides which are covalently linked to organic moieties, such as those described in WO 90/10448, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the and sense or sense oligonucleotide for the target nucleotide sequence.

Antisense or sense oligonucleotides may be introduced into a cell containing the target nucleic acid sequence by any gene transfer method, including, for example, $CaPO_4$-mediated DNA transfection, electroporation, or by using gene transfer vectors such as Epstein-Barr virus. Antisense or sense oligonucleotides are preferably introduced into a cell containing the target nucleic acid sequence by insertion of the antisense or sense oligonucleotide into a suitable retroviral vector, then contacting the cell with the retrovirus vector containing the inserted sequence, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see PCT Application US 90/02656).

Sense or antisense oligonucleotides also may be introduced into a cell containing the target nucleotide sequence by formation of a conjugate with a ligand binding molecule, as described in WO 91/04753. Suitable ligand binding molecules include, but are not limited to cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

In addition to the above, the following examples are provided to illustrate particular embodiments and not to limit the scope of the invention.

EXAMPLE 1

Isolating a Human Semaphorin Homologue Designated DCSema

Using sequence alignment techniques and comparative sequence analysis of ESTs, a human homologue of AHVY Sema semaphorin was identified as follows. The nucleotide sequence of viral A39R was used in a Unigene comparative sequence search. This search resulted in the identification of EST #151129 (accession #[HO2902], deposited Jun. 20. 1995. EST 151129 is a partial sequence having neither an initiating ATG nor a termination codon. EST 151129 has sequence homology to A39R and AHV sema.

EST 151129 was utilized to isolate and identify the native human DCSema as follows:

A tissue source of EST 151129 was identified using phage library screening methods and PCR primers based upon this EST sequence. Oligonucleotide PCR primers having the following nucleotide sequences were synthesized:

5'-TGCTGGAACCTGGTGAATGG-3' (SEQ ID NO:3)

5'-AGTGGAACAATGGCGTTTCC-3' (SEQ ID NO:4)

PCR isolation and amplification methodologies were carried out using a panel of human tissue cDNA phase libraries as templates for the PCR reactions.

Two of the phage libraries, human foreskin fibroblast and dermal fibroblast, were chosen for additional analysis. The libraries were plated according to established procedures. A radiolabeled probe was generated by incorporating $^{32}P$-dCTP in the amplification of a PCR product using the EST 151129 as a template. The PCR reaction mixture included 10 ng of EST151129 plasmid DNA, 50 pmoles of each PCR oligonucleotide primer identified below and specific for the 5end of EST 151129, 1X Amplitaq buffer (Perkin-Elmer Cetus), 1.25 mM of dATP, dGTP, dTIP, .001mM dCTP (Pharmacia, ), 150 $\mu$Ci $^{32}P$-dCTP, 0.5ul Amplitaq taq polymerase (Perkin-Elmer Cetus,) in a 100 $\mu$l final reaction volume. The PCR reaction cycles included one cycle at 94° C. for 5 min:twenty-five cycles at 94° C. for 1 min, 72° C. for 2 min and one cycle at 72° C. for 5 min using a Robocycler Gradient 40 (Stratagene, La Jolla. Calif.).

The primers used were as follows:

5'-TCCGCCCAGGGCCACCTAAGGAGCGGA-3' (SEQ ID NO:7)

5'-TGTGCGGCTCAGTCTGGCCAAAGTCCA-3' (SEQ ID NO:8)

Approximately $5 \times 10^5$ cpm/mL of purified probe was used to hybridize with the human dermal fibroblast library on nylon membrane filters in the same manner described in Example 5 for probing human foreskin fibroblast and human dermal fibroblast libraries.

A cDNA that overlapped with the 5' end of EST 151129 was isolated. Using sequence alignments it was determined that EST 151129 sequence included nucleotides 115–1536, encoding amino acids 39–512 of the full length peptide. The isolated cDNA provided nucleotides 1–114 and additional upstream non-coding nucleotides. These added nucleotides encode amino acids 1–38 of the full length human semaphorin, amino acid 1 being the initiating methionine.

In order to isolate cDNA overlapping the 3' end of EST 151129, another radiolabeled PCR probe was generated as described above but using PCR oligonucleotide primers specific for the 3end of EST 151129:

5'-AGCCAGGTGCCCCTGGACCT-3' (SEQ ID NO:9)

5'-CTCGAGGCCAAGAATTCGGC-3' (SEQ ID NO:10)

Approximately $5 \times 10^5$ cpm/mL of purified probe was used to hybridize with the human foreskin fibroblast library on nylon membrane filters following the hybridization and washing protocol described above. Three independent cDNA clones were isolated which overlapped with the 3' end of EST151129 and extended the 3' end of EST 151129 from nucleotide 1537 to 2001. The isolated clones contained additional downstream non-codina nucleotides. Nucleotides 1537–2001 translate into amino acids 513–666 of the full length peptide plus a stop codon. The full cDNA sequence of the human DCSema homologue is provided in SEQ ID NO:1. The encoded amino acid sequence is shown in SEQ ID NO:2.

EXAMPLE 2

Northern Blot Analysis for Tissue Expressing the Human Homologue

Radiolabeled probes derived from SEQ D NO:1 were used in Northern blot analyses of different human tissues to identify the tissue distribution of the human homologue of AHV Sema, designated DCSema.

Human poly A+ multiple tissue northern blots were purchased form Clontech Laboratories, Palo Alto, Calif. (Cat. #s 7760–1,7759–1, 7756–1, 757–1). The northern blot filters were prehybridized, probed, and washed according to manufacturer's instructions. The probe was an antisense riboprobe specific for EST 151129, an EST discovered using the viral AHV Sema sequence in sequence alignment analyses and comparative analysis methods. The template for the riboprobe was generated using PCR techniques and oligonucleotide primers that were designed to span nucleotides 613 to 978 of EST 151129(HO2902/H). The primers sequences were as follows:

5' Primer:
TCTACTACTT CTTCC (SEQ ID NO:5)
3' Primer
GGAATCCTAA TACGACTCAC TATAGGGAGG CGGGTTGGGA AGGC (SEQ ID NO:6)

The underlined portion of the downstream primer is a T7 site.

The riboprobe was generated using Ambion's MAXIscript SP6/T7 kit by combining 3 μL of RNAse free water, 2 μL 10 μL transcription buffer, 1 μL each of 10 mM dATP/dCTP/dGTP, 5 μL 5'/3' EST 151129 PCR Product, 5 μL Amersham [α$^{32}$P]UTP 10 mCi/mL, and 2 μL T7 RNA polymerase at room temperature. The combination was microfuged, spun briefly, and incubated at 37° C. for 30 minutes. Then 1 μL DNAse was added to the mixture and allowed to react for 15 minutes at 37° C. The reaction product was passed through two column volumes of G-25 (Boehringer). One microliter (1μL) of the riboprobe was counted in a scintillation counter for 1 minute to determine cpmi/μL.

After probing the northern blots, they were washed once for 30 minutes with 2×SSC, 0.05% SDS at 63° C. and three times for 30 minutes with 0.1×SSC, 0.1% SDS and then exposed to x-ray film. The developed film indicated that the human DCSema homologue is found in placenta, brain, spinal cord, testes and spleen. Weak hybridization signals were observed in skeletal muscle, lymph node, ovary, and bone marrow.

EXAMPLE 3

Preparing a DC-Sema/Fc Fusion Protein

This example describes preparing a DC-Sema/Fc DNA construct and subsequently expressing a DC-Sema/immunoglobulin Fc fusion protein referred to as DC-Sema/Fc. DNA encoding DC-Sema/Fc included a nucleotide sequence that encodes a murine IL-7 leader peptide, a FLAG™ octapeptide (described in U.S. Pat. No. 5,011,912), an Fc region of an immunoglobulin mutated to minimize binding to Fc receptor (described by Baum et al. Cir. Sh. 44:30, 1994), a flexible linker sequence and DNA encoding amino acids 45–666 of SEQ ID NO:2. An expression vector containing the leader sequence, FLAG, mutated hu IgG Fc and flexible linker was prepared using conventional enzyme cutting and ligation techniques. The resulting vector was then restricted with Spe 1 and Not1. The DC-Sema was inserted 5' to 3' after the flexible linker in a two-way ligation described below.

To prepare the DC-Sema DNA, three primer pairs were designed and used to amplify three DNA fragments. Two of the fragments were amplified from a human foreskin fibroblast library phage clone containing the 3' portion of the DCSema cDNA and one fragment was EST DNA (Research Genetics Imageclone ID #151129). The three amplified DNA fragments were combined in a PCR SOEing reaction to generate a DNA fragment encoding the entire peptide of DC-Sema (Horton et al., Biotechniques 20 8:528, 1990). In the final fragment, the upstream oligonucleotide primer introduced a Spe 1 site upstream of amino acid 45 of the DC-sema peptide. A downstream oligonucleotide primer introduced a Not1 site just downstream of the termination codon after amino acid 666.

The PCR fragment was then ligated into an expression vector (pDC409) containing the leader sequence. Flag® sequence, mutated human IgG Fc and a flexible linker region in a two-way ligation. The resulting DNA construct was transfected into the monkey kidney cell lines CV-1/EBNA. After 7 days of culture in medium containing 0.5% low immunoglobulin bovine serum, a solution of 0.2% azide was added to the supernatant and the supernatant was filtered through a 0.22 μm filter. Then approximately 1 L of culture supernatant was passed through a BioCad Protein A HPLC protein purification system using a 4.6×100 mm Protein A column (POROS 20A from PerSeptive Biosystems) at 10 mL/min. The Protein A column binds the Fc Portion of the fusion protein in the supernatant, immobilizing the fusion protein and allowing other components of the supernatant to pass through the column. The column was washed with 35 30 mL of PBS solution and bound fusion protein was eluted from the HPLC column with citric acid adjusted to pH 3.0. Eluted purified fusion protein was neutralized as it eluted using 1M HEPES solution at pH 7.4.

EXAMPLE 4

Preparing DC-Sema/polyHIS Fusion Protein

This example describes preparing a DC-Sema/polyHIS DNA construct and subsequently expressing a DCSema/poly histidine tagged protein referred to as DC-sema/polyHIS fusion protein. DNA encoding DC-sema/polyHIS comprises sequences encoding the DC-sema gene from amino acid 1 to amino acid 666 (no stop codon), followed by a factor Xa cleavage site, a FLAG® octapeptide, a string of six histidine residues and a stop codon. An expression vector containing the factor Xa cleavage site, flag, and polyHIS sequence was prepared using conventional enzyme cutting and fragment ligation techniques. The resulting vector was then restricted with SalI and SnaB1. The DCSema sequence was inserted 5' to 3' before the factor Xa cleavage site in a two-way ligation described below.

To prepare the DCSema DNA, three primer pairs were designed and used to amplify three DNA fragments. Two of the fragments were from phage DNA and one fragment was EST DNA (Research Genetics Imageclone ID #151129). The three amplified DNA framents were combined in a PCR SOEing reaction to generate a DNA fragment encoding the entire peptide of DCsema. This final DNA included a SalI site upstream of amino acid 1 of the DCSema peptide and a SnaBI site downstream of amino acid 666.

The PCR product was then ligated into an expression vector pDC409 containing the factor Xa cleavage site, flag, and polyHIS sequence in a two-way ligation. The resultant DNA construct (DCSema/polyHIS) was transiently transfected into the monkey cell line COS-1 (ATCC CRL-1650). Following a 7 day culture in medium containing 0.5% low immunoglobulin bovine serum, cell supernatants were harvested and a solution of 0.2% sodium azide was added to the supernatants. The supernatants were filtered through a 0.22 $\mu$m filter, concentrated 10 fold with a prep scale concentrator (Millipore. Bedford, Mass.) and purified on a BioCad HPLC protein purification equipped with a Nickel NTA Superflow self pack resin column (Qiagen, Santa Clarita, Calif.). After the supernatant passed through the column, the column was washed with Buffer A (20 mM NaPO4, pH7.4; 300 mMNaCl; 50 mM Imidazole). Bound protein was then eluted from the column using a gradient elution techniques. Fractions containing protein were collected and analyzed on a 4–20% SDS-PAGE reducing gel. Peaks containing the fusion protein were pooled, concentrated 2 fold, and then dialyzed in PBS. The resulting DCSema/polyHis fusion protein was then filtered through a 0.22 $\mu$m sterile filter and recovered.

EXAMPLE 5

Screening Cell Lines for Binding to DCSema

The DC-Sema/Fc fusion protein prepared as described in Example 3 was used to screen cell lines for binding using quantitative binding studies according to standard flow cytometry methodologies. For each cell line screened, the procedure involved incubating approximately 100,000 of the cells blocked with 2% FCS (fetal calf serum), 5% normal goat serum and 5% rabbit serum in PBS for 1 hour. Then the blocked cells were incubated with 5 $\mu$g/mL of DC-Sema/Fc fusion protein in 2% FCS, 5% goat serum and 5% rabbit serum in PBS. Following the incubation the sample was washed 2 times with FACS buffer (2% FCS in PBS) and then treated with mouse anti human Fc/biotin (purchased from Jackson Research) and SAPE (streptavidin-phycoerythrin purchased from Molecular Probes). This treatment causes the antihuman Fc/biotin to bind to any bound DC-Sema/Fc and the SAPE to bind to the anti human Fc/biotin resulting in a fluorescent identifying label on DC-Sema/Fc which is bound to cells. The cells were analyzed for any bound protein using fluorescent detection flow cytometry. Table 1 details the results of the flow cytometry studies. +indicates that binding was detected between the cell surface and DC-Sema. –indicates that no binding was detected between the cell surface and A39R.

TABLE I

| Cell Line | | DC-Sema Binding Result |
|---|---|---|
| CB23 | (Human Cord Blood B Cell Line) | + |
| MP-1 | (Human B Cell Lymphoma) | + |
| PB B | (Human Peripheral Blood B Cells) | + |
| U937 | (Human Monocyte-Type Cell) | + |
| W126 | (Human Lung Epithelium) | + |
| RAJI | (Burkitt's Lymphoma) | + |
| Primary Human Monocytes | | + |
| THP-1 | (Human Promonocytes) | + |

EXAMPLE 6

Monoclonal Antibodies to DC-Sema

This example illustrates a method for preparing antibodies to DC-Sema. Purified DC-Sema/Fc is prepared as described in Example 3 above. The purified protein is used to generate antibodies against DC-Sema as described in U.S. Pat. No. 4,411,993. Briefly, mice are immunized at 0, 2 and 6 weeks with 10 $\mu$g with DCSema/Fc. The primary immunization is prepared with TITERMAX adjuvant, from Vaxcell, Inc., and subsequent immunizations are prepared with incomplete Freund's adjuvant (IFA). At 11 weeks, the mice are IV boosted with 3–4 $\mu$g DCSema/Fc in PBS. Three days after the IV boost, splenocytes are harvested and fused with an Ag8.653 myeloma fusion partner using 50% aqueous PEG 1500 solution. Hybridoma supernatants are screened for DC-Sema antibodies by dot blot assay against DCSema/FC and an irrelevant Fc protein.

EXAMPLE 7

Cytokine Induction from Freshly Isolated Human Monocytes

Freshly isolated human monocytes were purified by first diluting 1:1 peripheral blood from healthy donors in low endotoxin PBS at pH 7.4 and room temperature. Then 35 mLs of the diluted blood was layered over 15 mLs of Isolymph (Gallard and Schlesinger Industries, Inc; Carle Place, N.Y.) and centrifuged at 2200 rpm for 25 minutes at room temperature. The plasma layers was reserved. The PBMC layer was harvested and washed three times to remove the Isolymph. The washed PBMC's were resuspended in X-Vivo 15 serum free media (BioWhittaker, Walkersville, Md.) and added to T175 flasks. The flasks had been previously coated with 2% Gelatin (Sigma, St. Louis, Mo.) and pre-treated for 30 minutes with the reserved plasma layer. The PBMC's were allowed to adhere for 90 minutes at 37° C., 5% $CO_2$ and then rinsed three times gently with 10 mL washes of low endotoxin PBS. Adhered monocytes were harvested by incubating the cells in Enzyme Free Dissociation Buffer (Gibco, BRL) and washing the cells multiple times in PBS. Monocytes were centrifuged at 2500 rpm for 5 minutes, counted, and set up in 24 well dishes at $5 \times 10^5$ cells/well in 1 mL. The cultures were 95% pure.

Purified monocytes were cultured for 7–9 days in the presence of 20 ng/mL GM-CSF and 100 ng/mL IL-4 in order to allow cells to differentiate to a more dendritic cell-like phenotype. On day 7–9, cultures were treated with 1 $\mu$g/mL DCSema/Fc fusion protein (see Example 3) or a control Fc protein, and the next day cells and supernatants were harvested for analyses.

The monocyte supernatants were examined for the presence of proinflammatory cytokines. In all donors tested, IL-6 and IL-8 was induced by DCSema protein. Heat inactivated DCSema and control proteins did not induce IL-6 or IL-8. Additionally, cytokine production was blocked by the inclusion of a mAb directed against DCSema.

The results of this experiment demonstrate that DCSema, or homologues of this protein, by interact with its receptor, can induce cytokine production by freshly isolated monocytes.

EXAMPLE 8

Monocyte Aggregation Studies

In order to examine human monocyte response to the interaction of a DCSema to its receptor on monocytes, monocytes were purified as described in Example 7 and DC-Sema/Fc fusion protein was prepared as described in Example 3. After incubating the DCSema/Fc fusion protein and purified, cultured monocytes for 20 hours, monocyte aggregation was observed.

This work confirms that the receptor for the DCSema of the present invention is expressed on monocytes and that the interaction between DCSema and it receptor results in monocyte aggregation. Similar to B cells, monocyte aggregation is indicative of their activation.

What is claimed is:

1. A method comprising assaying the binding of a DCSema polypeptide to a VESPR protein wherein the DCSema polypeptide comprises an amino acid sequence at least 80% identical to amino acids 45–666 of SEQ ID NO:2, wherein the percent identity is calculated using the GAP program with a unary comparison matrix, a 3.0 gap penalty, an additional 0.10 penalty for each symbol in each gap, and no penalty for end gaps.

2. The method of claim 1, wherein the VESPR protein is soluble.

3. The method of claim 2, wherein the soluble VESPR protein is conjugated to a drug, toxin, radionuclide chromophore and/or enzyme.

4. The method of claim 1, wherein the DCSema polypeptide is soluble.

5. The method of claim 4, wherein the soluble DCSema polypeptide is conjugated to a drug, toxin, radionuclide, chromophore and/or enzyme.

6. The method of claim 5, wherein the VESPR protein is expressed on a cell surface.

7. The method of claim 1, further comprising assaying inhibition of the binding of the DCSema polypeptide to the VESPR polypeptide with an antibody that immunospecifically recognizes the DCSema polypeptide.

8. The method of claim 1, wherein the DCSema polypeptide comprises amino acids 52–543 of SEQ ID NO:2.

9. The method of claim 8, wherein the DCSema polypeptide comprises amino acids 45–644 of SEQ ID NO:2.

* * * * *

SEQUENCE LISTING

<160> NUMBER OF SEQ ID NOS: 10

<210> SEQ ID NO 1
<211> LENGTH: 2001
<212> TYPE: DNA
<213> ORGANISM: Homo sapiens
<220> FEATURE:
<221> NAME/KEY: CDS
<222> LOCATION: (1)..(2001)
<223> OTHER INFORMATION:

<400> SEQUENCE: 1

| | | | | | | | | | | | | | | | | |
|---|---|---|---|---|---|---|---|---|---|---|---|---|---|---|---|---|
| atg | acg | cct | cct | ccg | ccc | gga | cgt | gcc | gcc | ccc | agc | gca | ccg | cgc | gcc | 48 |
| Met | Thr | Pro | Pro | Pro | Gly | Arg | Ala | Ala | Pro | Ser | Ala | Pro | Arg | Ala | | |
| 1 | | | | 5 | | | | | 10 | | | | | 15 | | |
| cgc | gtc | cct | ggc | ccg | ccg | gct | cgg | ttg | ggg | ctt | ccg | ctg | cgg | ctg | cgg | 96 |
| Arg | Val | Pro | Gly | Pro | Pro | Ala | Arg | Leu | Gly | Leu | Pro | Leu | Arg | Leu | Arg | |
| | | | | 20 | | | | | 25 | | | | | 30 | | |
| ctg | ctg | ctg | ctg | ctt | tgg | gcg | gcc | gcc | tcc | gcc | cag | ggc | cac | cta | | 144 |
| Leu | Leu | Leu | Leu | Leu | Trp | Ala | Ala | Ala | Ser | Ala | Gln | Gly | His | Leu | | |
| | | | 35 | | | | | 40 | | | | | 45 | | | |
| agg | agc | gga | ccc | cgc | atc | ttc | gcc | gtc | tgg | aaa | ggc | cat | gta | ggg | cag | 192 |
| Arg | Ser | Gly | Pro | Arg | Ile | Phe | Ala | Val | Trp | Lys | Gly | His | Val | Gly | Gln | |
| | | 50 | | | | | 55 | | | | | 60 | | | | |
| gac | cgg | gtg | gac | ttt | ggc | cag | act | gag | ccg | cac | acg | gtg | ctt | ttc | cac | 240 |
| Asp | Arg | Val | Asp | Phe | Gly | Gln | Thr | Glu | Pro | His | Thr | Val | Leu | Phe | His | |
| 65 | | | | | 70 | | | | | 75 | | | | | 80 | |
| gag | cca | ggc | agc | tcc | tct | gtg | tgg | gtg | gga | gga | cgt | ggc | aag | gtc | tac | 288 |
| Glu | Pro | Gly | Ser | Ser | Ser | Val | Trp | Val | Gly | Gly | Arg | Gly | Lys | Val | Tyr | |
| | | | | 85 | | | | | 90 | | | | | 95 | | |
| ctc | ttt | gac | ttc | ccc | gag | ggc | aag | aac | gca | tct | gtg | cgc | acg | gtg | aat | 336 |
| Leu | Phe | Asp | Phe | Pro | Glu | Gly | Lys | Asn | Ala | Ser | Val | Arg | Thr | Val | Asn | |
| | | | | 100 | | | | | 105 | | | | | 110 | | |
| atc | ggc | tcc | aca | aag | ggg | tcc | tgt | ctg | gat | aag | cgg | gac | tgc | gag | aac | 384 |
| Ile | Gly | Ser | Thr | Lys | Gly | Ser | Cys | Leu | Asp | Lys | Arg | Asp | Cys | Glu | Asn | |
| | | | 115 | | | | | 120 | | | | | 125 | | | |
| tac | atc | act | ctc | ctg | gag | agg | cgg | agt | gag | ggg | ctg | ctg | gcc | tgt | ggc | 432 |
| Tyr | Ile | Thr | Leu | Leu | Glu | Arg | Arg | Ser | Glu | Gly | Leu | Leu | Ala | Cys | Gly | |
| | | 130 | | | | | 135 | | | | | 140 | | | | |
| acc | aac | gcc | cgg | cac | ccc | agc | tgc | tgg | aac | ctg | gtg | aat | ggc | act | gtg | 480 |
| Thr | Asn | Ala | Arg | His | Pro | Ser | Cys | Trp | Asn | Leu | Val | Asn | Gly | Thr | Val | |
| 145 | | | | | 150 | | | | | 155 | | | | | 160 | |
| gtg | cca | ctt | ggc | gag | atg | aga | ggc | tac | gcc | ccc | ttc | agc | ccg | gac | gag | 528 |
| Val | Pro | Leu | Gly | Glu | Met | Arg | Gly | Tyr | Ala | Pro | Phe | Ser | Pro | Asp | Glu | |
| | | | | 165 | | | | | 170 | | | | | 175 | | |
| aac | tcc | ctg | gtt | ctg | ttt | gaa | ggg | gac | gag | gtg | tat | tcc | acc | atc | cgg | 576 |
| Asn | Ser | Leu | Val | Leu | Phe | Glu | Gly | Asp | Glu | Val | Tyr | Ser | Thr | Ile | Arg | |
| | | | | 180 | | | | | 185 | | | | | 190 | | |
| aag | cag | gaa | tac | aat | ggg | aag | atc | cct | cgg | ttc | cgc | cgc | atc | cgg | ggc | 624 |
| Lys | Gln | Glu | Tyr | Asn | Gly | Lys | Ile | Pro | Arg | Phe | Arg | Arg | Ile | Arg | Gly | |
| | | | 195 | | | | | 200 | | | | | 205 | | | |
| gag | agt | gag | ctg | tac | acc | agt | gat | act | gtc | atg | cag | aac | cca | cag | ttc | 672 |
| Glu | Ser | Glu | Leu | Tyr | Thr | Ser | Asp | Thr | Val | Met | Gln | Asn | Pro | Gln | Phe | |
| | | 210 | | | | | 215 | | | | | 220 | | | | |
| atc | aaa | gcc | acc | atc | gtg | cac | caa | gac | cag | gct | tac | gat | gac | aag | atc | 720 |
| Ile | Lys | Ala | Thr | Ile | Val | His | Gln | Asp | Gln | Ala | Tyr | Asp | Asp | Lys | Ile | |
| 225 | | | | | 230 | | | | | 235 | | | | | 240 | |
| tac | tac | ttc | ttc | cga | gag | gac | aat | cct | gac | aag | aat | cct | gag | gct | cct | 768 |
| Tyr | Tyr | Phe | Phe | Arg | Glu | Asp | Asn | Pro | Asp | Lys | Asn | Pro | Glu | Ala | Pro | |
| | | | 245 | | | | | 250 | | | | | 255 | | | |

```
ctc aat gtg tcc cgt gtg gcc cag ttg tgc agg ggg gac cag ggt ggg      816
Leu Asn Val Ser Arg Val Ala Gln Leu Cys Arg Gly Asp Gln Gly Gly
            260                 265                 270 gaa agt tca ctg tca gtc tcc aag tgg aac act ttt ctg aaa gcc atg      864
Glu Ser Ser Leu Ser Val Ser Lys Trp Asn Thr Phe Leu Lys Ala Met
            275                 280                 285 ctg gta tgc agt gat gct gcc acc aac aag aac ttc aac agg ctg caa      912
Leu Val Cys Ser Asp Ala Ala Thr Asn Lys Asn Phe Asn Arg Leu Gln
        290                 295                 300 gac gtc ttc ctg ctc cct gac ccc agc ggc cag tgg agg gac acc agg      960
Asp Val Phe Leu Leu Pro Asp Pro Ser Gly Gln Trp Arg Asp Thr Arg
305                 310                 315                 320 gtc tat ggt gtt ttc tcc aac ccc tgg aac tac tca gcc gtc tgt gtg     1008
Val Tyr Gly Val Phe Ser Asn Pro Trp Asn Tyr Ser Ala Val Cys Val
                325                 330                 335 tat tcc ctc ggt gac att gac aag gtc ttc cgt acc tcc tca ctc aag     1056
Tyr Ser Leu Gly Asp Ile Asp Lys Val Phe Arg Thr Ser Ser Leu Lys
                    340                 345                 350 ggc tac cac tca agc ctt ccc aac ccg cgg cct ggc aag tgc ctc cca     1104
Gly Tyr His Ser Ser Leu Pro Asn Pro Arg Pro Gly Lys Cys Leu Pro
            355                 360                 365 gac cag cag ccg ata ccc aca gag acc ttc cag gtg gct gac cgt cac     1152
Asp Gln Gln Pro Ile Pro Thr Glu Thr Phe Gln Val Ala Asp Arg His
        370                 375                 380 cca gag gtg gcg cag agg gtg gag ccc atg ggg cct ctg aag acg cca     1200
Pro Glu Val Ala Gln Arg Val Glu Pro Met Gly Pro Leu Lys Thr Pro
385                 390                 395                 400 ttg ttc cac tct aaa tac cac tac cag aaa gtg gcc gtt cac cgc atg     1248
Leu Phe His Ser Lys Tyr His Tyr Gln Lys Val Ala Val His Arg Met
                405                 410                 415 caa gcc agc cac ggg gag acc ttt cat gtg ctt tac cta act aca gac     1296
Gln Ala Ser His Gly Glu Thr Phe His Val Leu Tyr Leu Thr Thr Asp
                    420                 425                 430 agg ggc act atc cac aag gtg gtg gaa ccg ggg gag cag gag cac agc     1344
Arg Gly Thr Ile His Lys Val Val Glu Pro Gly Glu Gln Glu His Ser
            435                 440                 445 ttc gcc ttc aac atc atg gag atc cag ccc ttc cgc cgc gcg gct gcc     1392
Phe Ala Phe Asn Ile Met Glu Ile Gln Pro Phe Arg Arg Ala Ala Ala
        450                 455                 460 atc cag acc atg tcg ctg gat gct gag cgg agg aag ctg tat gtg agc     1440
Ile Gln Thr Met Ser Leu Asp Ala Glu Arg Arg Lys Leu Tyr Val Ser
465                 470                 475                 480 tcc cag tgg gag gtg agc cag gtg ccc ctg gac ctg tgt gag gtc tat     1488
Ser Gln Trp Glu Val Ser Gln Val Pro Leu Asp Leu Cys Glu Val Tyr
                485                 490                 495 ggc ggg ggc tgc cac ggt tgc ctc atg tcc cga gac ccc tac tgc ggc     1536
Gly Gly Gly Cys His Gly Cys Leu Met Ser Arg Asp Pro Tyr Cys Gly
                    500                 505                 510 tgg gac cag ggc cgc tgc atc tcc atc tac agc tcc gaa cgg tca gtg     1584
Trp Asp Gln Gly Arg Cys Ile Ser Ile Tyr Ser Ser Glu Arg Ser Val
            515                 520                 525 ctg caa tcc att aat cca gcc gag cca cac aag gag tgt ccc aac ccc     1632
Leu Gln Ser Ile Asn Pro Ala Glu Pro His Lys Glu Cys Pro Asn Pro
        530                 535                 540 aaa cca gac aag gcc cca ctg cag aag gtt tcc ctg gcc cca aac tct     1680
Lys Pro Asp Lys Ala Pro Leu Gln Lys Val Ser Leu Ala Pro Asn Ser
545                 550                 555                 560 cgc tac tac ctg agc tgc ccc atg gaa tcc cgc cac gcc acc tac tca     1728
Arg Tyr Tyr Leu Ser Cys Pro Met Glu Ser Arg His Ala Thr Tyr Ser
```

|  |  |  |  |  | 565 |  |  |  | 570 |  |  |  |  | 575 |  |  |
|---|---|---|---|---|---|---|---|---|---|---|---|---|---|---|---|---|
| tgg | cgc | cac | aag | gag | aac | gtg | gag | cag | agc | tgc | gaa | cct | ggt | cac | cag | 1776 |
| Trp | Arg | His | Lys | Glu | Asn | Val | Glu | Gln | Ser | Cys | Glu | Pro | Gly | His | Gln |  |
|  |  |  | 580 |  |  |  |  | 585 |  |  |  |  | 590 |  |  |  |
| agc | ccc | aac | tgc | atc | ctg | ttc | atc | gag | aac | ctc | acg | gcg | cag | cag | tac | 1824 |
| Ser | Pro | Asn | Cys | Ile | Leu | Phe | Ile | Glu | Asn | Leu | Thr | Ala | Gln | Gln | Tyr |  |
|  |  | 595 |  |  |  |  | 600 |  |  |  |  | 605 |  |  |  |  |
| ggc | cac | tac | ttc | tgc | gag | gcc | cag | gag | ggc | tcc | tac | ttc | cgc | gag | gct | 1872 |
| Gly | His | Tyr | Phe | Cys | Glu | Ala | Gln | Glu | Gly | Ser | Tyr | Phe | Arg | Glu | Ala |  |
|  | 610 |  |  |  |  | 615 |  |  |  |  | 620 |  |  |  |  |  |
| cag | cac | tgg | cag | ctg | ctg | ccc | gag | gac | ggc | atc | atg | gcc | gag | cac | ctg | 1920 |
| Gln | His | Trp | Gln | Leu | Leu | Pro | Glu | Asp | Gly | Ile | Met | Ala | Glu | His | Leu |  |
| 625 |  |  |  |  | 630 |  |  |  |  | 635 |  |  |  |  | 640 |  |
| ctg | ggt | cat | gcc | tgt | gcc | ctg | gct | gcc | tcc | ctc | tgg | ctg | ggg | gtg | ctg | 1968 |
| Leu | Gly | His | Ala | Cys | Ala | Leu | Ala | Ala | Ser | Leu | Trp | Leu | Gly | Val | Leu |  |
|  |  |  |  | 645 |  |  |  |  | 650 |  |  |  |  | 655 |  |  |
| ccc | aca | ctc | act | ctt | ggc | ttg | ctg | gtc | cac | tag |  |  |  |  |  | 2001 |
| Pro | Thr | Leu | Thr | Leu | Gly | Leu | Leu | Val | His |  |  |  |  |  |  |  |
|  |  |  | 660 |  |  |  |  | 665 |  |  |  |  |  |  |  |  |

<210> SEQ ID NO 2
<211> LENGTH: 666
<212> TYPE: PRT
<213> ORGANISM: Homo sapiens

<400> SEQUENCE: 2

```
Met Thr Pro Pro Pro Gly Arg Ala Ala Pro Ser Ala Pro Arg Ala
1               5                   10                  15

Arg Val Pro Gly Pro Pro Ala Arg Leu Gly Leu Pro Leu Arg Leu Arg
            20                  25                  30

Leu Leu Leu Leu Leu Trp Ala Ala Ala Ser Ala Gln Gly His Leu
            35                  40                  45

Arg Ser Gly Pro Arg Ile Phe Ala Val Trp Lys Gly His Val Gly Gln
        50                  55                  60

Asp Arg Val Asp Phe Gly Gln Thr Glu Pro His Thr Val Leu Phe His
65                  70                  75                  80

Glu Pro Gly Ser Ser Ser Val Trp Val Gly Arg Gly Lys Val Tyr
                85                  90                  95

Leu Phe Asp Phe Pro Glu Gly Lys Asn Ala Ser Val Arg Thr Val Asn
            100                 105                 110

Ile Gly Ser Thr Lys Gly Ser Cys Leu Asp Lys Arg Asp Cys Glu Asn
            115                 120                 125

Tyr Ile Thr Leu Leu Glu Arg Arg Ser Glu Gly Leu Leu Ala Cys Gly
        130                 135                 140

Thr Asn Ala Arg His Pro Ser Cys Trp Asn Leu Val Asn Gly Thr Val
145                 150                 155                 160

Val Pro Leu Gly Glu Met Arg Gly Tyr Ala Pro Phe Ser Pro Asp Glu
                165                 170                 175

Asn Ser Leu Val Leu Phe Glu Gly Asp Glu Val Tyr Ser Thr Ile Arg
            180                 185                 190

Lys Gln Glu Tyr Asn Gly Lys Ile Pro Arg Phe Arg Arg Ile Arg Gly
            195                 200                 205

Glu Ser Glu Leu Tyr Thr Ser Asp Thr Val Met Gln Asn Pro Gln Phe
        210                 215                 220

Ile Lys Ala Thr Ile Val His Gln Asp Gln Ala Tyr Asp Asp Lys Ile
225                 230                 235                 240
```

```
Tyr Tyr Phe Phe Arg Glu Asp Asn Pro Asp Lys Asn Pro Glu Ala Pro
                245                 250                 255

Leu Asn Val Ser Arg Val Ala Gln Leu Cys Arg Gly Asp Gln Gly Gly
            260                 265                 270

Glu Ser Ser Leu Ser Val Ser Lys Trp Asn Thr Phe Leu Lys Ala Met
        275                 280                 285

Leu Val Cys Ser Asp Ala Ala Thr Asn Lys Asn Phe Asn Arg Leu Gln
    290                 295                 300

Asp Val Phe Leu Leu Pro Asp Pro Ser Gly Gln Trp Arg Asp Thr Arg
305                 310                 315                 320

Val Tyr Gly Val Phe Ser Asn Pro Trp Asn Tyr Ser Ala Val Cys Val
                325                 330                 335

Tyr Ser Leu Gly Asp Ile Asp Lys Val Phe Arg Thr Ser Ser Leu Lys
            340                 345                 350

Gly Tyr His Ser Ser Leu Pro Asn Pro Arg Pro Gly Lys Cys Leu Pro
        355                 360                 365

Asp Gln Gln Pro Ile Pro Thr Glu Thr Phe Gln Val Ala Asp Arg His
    370                 375                 380

Pro Glu Val Ala Gln Arg Val Glu Pro Met Gly Pro Leu Lys Thr Pro
385                 390                 395                 400

Leu Phe His Ser Lys Tyr His Tyr Gln Lys Val Ala Val His Arg Met
                405                 410                 415

Gln Ala Ser His Gly Glu Thr Phe His Val Leu Tyr Leu Thr Thr Asp
            420                 425                 430

Arg Gly Thr Ile His Lys Val Val Glu Pro Gly Glu Gln Glu His Ser
            435                 440                 445

Phe Ala Phe Asn Ile Met Glu Ile Gln Pro Phe Arg Arg Ala Ala Ala
    450                 455                 460

Ile Gln Thr Met Ser Leu Asp Ala Glu Arg Arg Lys Leu Tyr Val Ser
465                 470                 475                 480

Ser Gln Trp Glu Val Ser Gln Val Pro Leu Asp Leu Cys Glu Val Tyr
                485                 490                 495

Gly Gly Gly Cys His Gly Cys Leu Met Ser Arg Asp Pro Tyr Cys Gly
            500                 505                 510

Trp Asp Gln Gly Arg Cys Ile Ser Ile Tyr Ser Ser Glu Arg Ser Val
        515                 520                 525

Leu Gln Ser Ile Asn Pro Ala Glu Pro His Lys Glu Cys Pro Asn Pro
    530                 535                 540

Lys Pro Asp Lys Ala Pro Leu Gln Lys Val Ser Leu Ala Pro Asn Ser
545                 550                 555                 560

Arg Tyr Tyr Leu Ser Cys Pro Met Glu Ser Arg His Ala Thr Tyr Ser
                565                 570                 575

Trp Arg His Lys Glu Asn Val Glu Gln Ser Cys Glu Pro Gly His Gln
            580                 585                 590

Ser Pro Asn Cys Ile Leu Phe Ile Glu Asn Leu Thr Ala Gln Gln Tyr
        595                 600                 605

Gly His Tyr Phe Cys Glu Ala Gln Glu Gly Ser Tyr Phe Arg Glu Ala
    610                 615                 620

Gln His Trp Gln Leu Leu Pro Glu Asp Gly Ile Met Ala Glu His Leu
625                 630                 635                 640

Leu Gly His Ala Cys Ala Leu Ala Ala Ser Leu Trp Leu Gly Val Leu
                645                 650                 655

Pro Thr Leu Thr Leu Gly Leu Leu Val His
```

<210> SEQ ID NO 3
<211> LENGTH: 20
<212> TYPE: DNA
<213> ORGANISM: Artificial Sequence
<220> FEATURE:
<223> OTHER INFORMATION: PRIMER

<400> SEQUENCE: 3
tgctggaacc tggtgaatgg                                          20

<210> SEQ ID NO 4
<211> LENGTH: 20
<212> TYPE: DNA
<213> ORGANISM: Artificial Sequence
<220> FEATURE:
<223> OTHER INFORMATION: PRIMER

<400> SEQUENCE: 4
agtggaacaa tggcgtcttc                                          20

<210> SEQ ID NO 5
<211> LENGTH: 15
<212> TYPE: DNA
<213> ORGANISM: Artificial Sequence
<220> FEATURE:
<223> OTHER INFORMATION: PRIMER

<400> SEQUENCE: 5
tctactactt cttcc                                               15

<210> SEQ ID NO 6
<211> LENGTH: 44
<212> TYPE: DNA
<213> ORGANISM: Artificial Sequence
<220> FEATURE:
<223> OTHER INFORMATION: PRIMER

<400> SEQUENCE: 6
ggaatcctaa tacgactcac tatagggagg cgggttggga aggc               44

<210> SEQ ID NO 7
<211> LENGTH: 27
<212> TYPE: DNA
<213> ORGANISM: Artificial Sequence
<220> FEATURE:
<223> OTHER INFORMATION: PRIMER

<400> SEQUENCE: 7
tccgcccagg gccacctaag gagcgga                                  27

<210> SEQ ID NO 8
<211> LENGTH: 27
<212> TYPE: DNA
<213> ORGANISM: Artificial Sequence
<220> FEATURE:
<223> OTHER INFORMATION: PRIMER

<400> SEQUENCE: 8
tgtgcggctc agtctggcca aagtcca                                  27

<210> SEQ ID NO 9
<211> LENGTH: 20
<212> TYPE: DNA
<213> ORGANISM: Artificial Sequence

```
<220> FEATURE:
<223> OTHER INFORMATION: PRIMER

<400> SEQUENCE: 9
agccaggtgc ccctggacct                                               20

<210> SEQ ID NO 10
<211> LENGTH: 20
<212> TYPE: DNA
<213> ORGANISM: Artificial Sequence
<220> FEATURE:
<223> OTHER INFORMATION: PRIMER

<400> SEQUENCE: 10
ctcgaggcca agaattcggc                                               20
```